United States Patent [19]

Colle et al.

[11] Patent Number: 4,594,353

[45] Date of Patent: Jun. 10, 1986

[54] AZOLYL-FURAN-DERIVATIVES HAVING FUNGICIDE ACTIVITY

[75] Inventors: Roberto Colle, Basiglio; Franco Gozzo, S. Donato Milanese; Luigi Mirenna, Milan, all of Italy

[73] Assignee: Montedison S.p.A., Milan, Italy

[21] Appl. No.: 593,278

[22] Filed: Mar. 26, 1984

[30] Foreign Application Priority Data

Mar. 31, 1983 [IT] Italy ........................... 20406 A/83

[51] Int. Cl.$^4$ .................. A01N 43/50; A01N 43/653; C07D 407/04
[52] U.S. Cl. ................................. 514/383; 514/397; 548/336; 548/262
[58] Field of Search .............. 548/262, 336; 424/269, 424/273 R; 514/397, 383

[56] References Cited

U.S. PATENT DOCUMENTS

3,557,005 1/1971 Broaddus .................... 549/480

FOREIGN PATENT DOCUMENTS

8303096 9/1983 World Int. Prop. O. .......... 548/336
2122997 1/1984 United Kingdom ............ 548/336

*Primary Examiner*—Alton D. Rollins
*Attorney, Agent, or Firm*—Morgan, Finnegan, Pine, Foley & Lee

[57] ABSTRACT

There are disclosed compounds of formula:

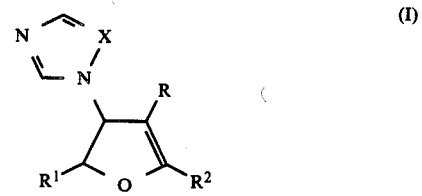

wherein R is selected from the group consisting of H, an alkyl, and alkenyl, an alkynyl, an alkoxyl, a phenyl, a phenoxy, an alkoxycarbonyl, an alkylcarbonyl, a benzoyl and a cyano group; $R^1$ and $R^2$ are each selected from the group consisting of an alkyl, an alkenyl, an alkynyl, a phenyl, an alkoxycarbonyl, an alkylcarbonyl and a cyano group; or R and $R^2$ together form an ortho-condensed benzene ring; X=CH or N.

The compounds of formula I are endowed with fungicide activity against phytopathogenous fungi.

8 Claims, No Drawings

AZOLYL-FURAN-DERIVATIVES HAVING FUNGICIDE ACTIVITY

BACKGROUND - FIELD OF INVENTION

This invention relates to novel furan-derivative compounds and their method of preparation, said compounds being particularly useful as a fungicide in combating fungus infection.

SUMMARY OF INVENTION

It is an object of this invention to provide novel furan-derivatives.

A further object of this invention is to provide furan-derivatives which exhibit highly desirable fungicidal activity.

It has been found that the objects of this invention may be realized by providing furan-derivatives having fungicide activity and more precisely it relates to furan-derivatives substituted in position 3 (or 4) by a heterocyclic radical deriving from imidazole or from 1,2,4-triazole, endowed with fungicide activity against phytopathogenous fungi and to the use thereof in the agriculture field for protecting useful crops against the fungus infections.

According to the rules of chemical nomenclature, a substituent Y in the position of the furan ring, as shown by the present formula,

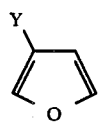

is indicated to be in position 3 or 4 depending on the optional presence of other substituents in different positions of the ring and on the nature thereof.

For simplicity in the present context, position 3 is assigned to the heterocyclic substituent (imidazole or 1,2,4-triazole); it is, however, understood that for some compounds of the invention a more correct nomenclature should assign position 4 to the heterocyclic substituent.

The novel furan derivatives of the present invention, have the general formula:

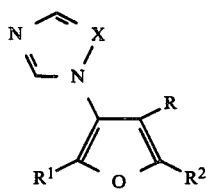

I wherein
X represents a nitrogen atom or a CH group;
R is selected from the group consisting of a hydrogen atom, an alkyl group having from 1 to 4 carbon atoms; an alkenyl group or an alkenyl group having from 2 to 5 carbon atoms; an alkoxyl group having from 1 to 4 carbon atoms; a phenyl group or a phenoxy group optionally substituted by one or more groups selected from the group consisting of halogen atoms, alkyl groups having from 1 to 4 carbon atoms, a nitro group; an alkoxycarbonyl having from 1 to 4 carbon atoms in the alkoxy part, alkylcarbonyl group having from 1 to 4 carbon atoms in the alkyl part; a benzoyl and a cyano group;

$R^1$ and $R^2$ (equal to or different from each other) are each selected from the group consisting of an alkyl group having from 1 to 4 carbon atoms; an alkenyl group having from 2 to 5 carbon atoms, an alkynyl group having from 2 to 5 carbon atoms; a phenyl group optionally substituted by one or two groups selected from the group consisting of halogen atoms, alkyl groups having from 1 to 4 carbon atoms, alkoxyl groups having from 1 to 4 carbon atoms and a nitro group; an alkoxycarbonyl group, an alkylcarbonyl group having from 1 to 4 carbon atoms in the alkyl part and a cyano group; or R and $R^2$ form together a benzene ring orthocondensed with the furan ring.

The compounds of formula 1 are endowed with a high fungicide activity and with other properties hereinafter described, which allow the use of such compounds in agriculture field for protecting useful cultivations against the action of phytopathogenous fungi.

The preparation of the compounds of formula I, that forms a further object of the present invention, is carried out according to the methods hereinafter described (symbols R, $R^1$, $R^2$ and X have the same meanings reported for formula I, unless otherwise specified).

A general process of synthesis, that can be carried out for all the compounds of formula I, wherein R and $R^2$ are not combined to form the orthocondensed benzene ring, consists in subjecting to cyclisation the diketones of formula II in the presence of a dehydrating agent, according to reaction 1

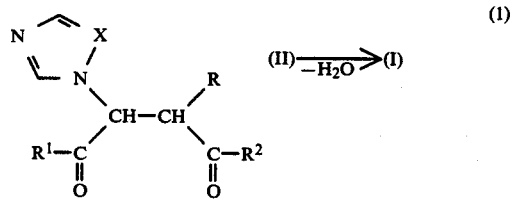

(1)

The diketones of formula II, wherein X is a nitrogen atom, and the preparation processes thereof have been disclosed in copending Italian patent applications No. 21.665 A/82 and No. 25.048 A/82. The compounds of formula II wherein X is a CH group, are obtained according to the reactions described in the above mentioned patent applications.

More particularly, the diketones of formula II, wherein X is a nitrogen atom, are obtained by adding 1,2,4-triazole to alpha, beta-unsaturated ketones of formula $R^1$—CO—CH=C(R)CO—$R^2$ in an inert solvent such as aromatic hydrocarbons, in the presence of a catalytic amount of an organic base, for instance a tertiary amine.

The diketones, wherein X is a CH group, are obtained according to the above process but using imidazole instead of 1,2,4-triazole.

Reaction 1 is carried out with good yields in acetic anhydride as solvent and in the presence of catalytic amounts of a strong acid (for instance concentrated $H_2SO_4$) at the reflux temperature of the reaction mixture.

Alternatively, reaction 1 can be carried out by using $P_2O_5$ or $TiCl_4$ as dehydrating agent in a suitable solvent such as a polychloro-alkane.

The synthesis of the compounds of formula I, wherein R and R² are not linked to form a ring, can be also carried out according to procedures different from the one indicated in reaction 1, for instance according to the process described in the following reaction 2.

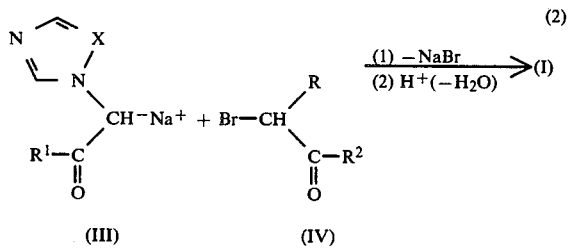

The compounds of formula III are the sodium salts of α-triazolyl (or imidazolyl) ketones, which are known compounds or can be easily prepared according to known techniques.

The α-bromo-ketones of formula IV are known compounds as well. Reaction 2 is carried out by reacting sodium salt III with bromo-derivative IV in an aprotic polar solvent (dimethylformamide or dimethylsulfoxide) and by subjecting the reaction product to a dehydration reaction, according to modalities analogous to the ones described for reaction 1. The compounds of formula I, wherein R and R² form together a benzene ring orthocondensed with the furan ring can be indicated by the following formula I-A

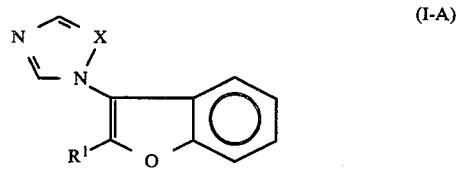

Their preparation is carried out according to the following reactions:

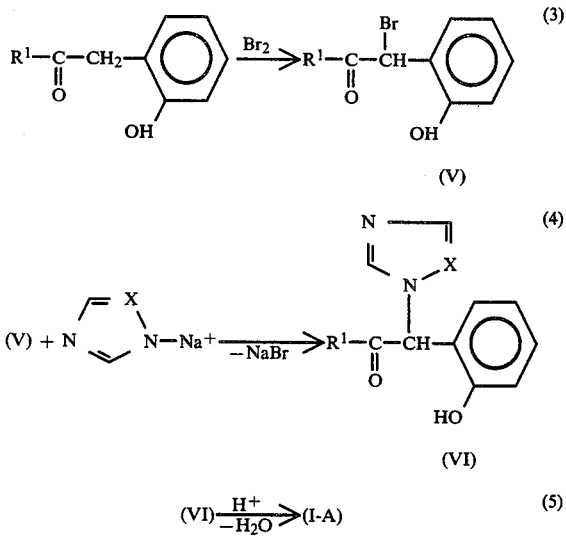

Reaction 3 consists in subjecting to a radical bromination a 2-hydroxybenzyl-ketone and falls within the normal process of bromination of activated benzyl groups. Reaction 4 is also of conventional type in the chemistry of azole alkylation. Reaction 5 is carried out according to the procedure disclosed in literature [*Acta Chim. Scan.* 10, 1422 (1956)] for the cyclization of 2-hydroxy-desoxybenzoin to 2-phenyl-benzofuran. As mentioned hereinbefore, the compounds of formula I are endowed with a high fungicide activity.

They possess a wide action spectrum, as they are active against phytopathogenous fungi belonging to various genera of numerous families such as for instance Piricularia, Puccinia, Erysiphe, Sphaerotheca, Botrytis, Phytophtora, Venturia, Fusarium, Plasmopara, Peronospore, Pythium and still others.

Therefore, the compounds of formula I are useful for fighting numerous plant diseases and they are particularly active against those diseases which are generally known as oidium and rust.

As antioidic compounds, the compounds according to the invention result to be endowed with a very high or complete activity even at extremely low doses.

Furthermore, the compounds of formula I possess other positive characteristics, such as fungicide action having both preventive and curative character and a complete compatibility with the plants to be protected against fungus infections. Owing to the high fungicide activity coupled with the above mentioned positive characteristics, the fungicide compounds which are the object of the present invention may be used for protecting quite a number of useful crops from fungus action; among these useful crops we can cite: vine, rice, Gramineae, tomato, tobacco and other Solanaceae, horticultural cultivations, strawberries, Cucuribitaceae, fruit trees and ornamental plants. They can be used for protecting food stuffs as well.

For the practical uses in agriculture it is often useful to have available fungicide compositions containing one or more compounds of formula I as active ingredient.

Such compositions which, according to the normal formulative practice, are in the form of dry powders, wettable powders, emulsifiable concentrates, pastes, granular formulates, etc., consist of one or more compounds of formula I as active ingredient, of a solid or liquid carrier and optionally of other additives such as, for instance, surfactants, wetting agents, dispersing agents, suspending agents, etc.

If desired, it is possible to add to the compositions of the invention, other compatible active substances such as other fungicides, herbicides, phytogrowth regulators, fertilizers and insecticides.

The dose of active substance to be used varies as a function of different factors such as the kind, the degree and the stadium of the fungus infection, the cultivation to be protected, the specific effectiveness of the considered compound of formula I, climatic and environmental factors.

Owing to the high fungicidal activity of the compounds of formula I, it is generally sufficient to use amounts of active substance ranging from 10 to 2000 g/ha, preferably from 100 to 1500 g/ha.

The following examples are given to better illustrate the invention.

EXAMPLE I

Preparation of 2,4,5 triphenyl-3-(1,2,4-triazolyl-1)-furan (Compound No. 1)

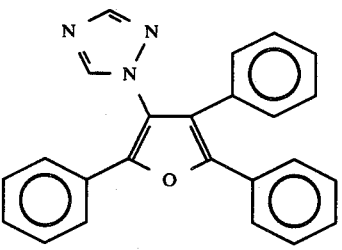

15,24 g (0.04 moles) of 1,2,4-triphenyl-3-(1,2,4-triazolyl) butan-1,4-dione (described in Italian patent application No. 25,048A/82) were suspended in 100 ml of acetic anhydride.

After addition of 1.2 ml of concentrated $H_2SO_4$, the suspension was reflux heated for 3 hours.

The reaction mixture, after having been cooled down to room temperature, was poured into 1.5 l of water and ice kept under stirring.

A precipitate was separated, that after about 1 hour, was collected by filtration and washed with water till a neutral pH and dried in the air.

The solid was recrystallized from ethyl alcohol to yield 10 g of the desired product (compound No. 1) having a melting point (m.p.)=180°-182° C.

IR: significant bands at 1595, 1500, 1400, 1440 and 1370 cm$^{-1}$.

EXAMPLE 2

Preparation of 2.5-diphenyl-3-(1,2,4-triazolyl-1)-furan (Compound No. 2).

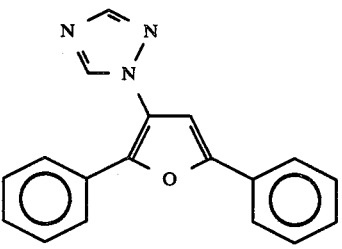

7.5 g (0.04 moles) of 2-(1,2,4-triazolyl-1)-acetophenone were dissolved in 50 ml of dimethylformamide (DMF) and the solution was added drop by drop to a suspension of 1.92 q of NaH at 50% in mineral oil kept under stirring at 5° C.

After further 30 seconds of stirring at the same temperature the resulting mixture was added by dropping under nitrogen into a solution containing 8 g (0.04 moles) of 2-bromo-acetophenone in 30 ml of DMF, kept under stirring at a temperature of 0°-5° C.

When the addition was over, the reaction mixture was kept at room temperature for four hours.

The solvent was then removed by evaporation at reduced pressure and the residue was diluted with 150 ml of acetic anhydride.

After addition of 1 ml of concentrated $H_2SO_4$, the mixture was reflux heated for three hours and, after having been cooled down to room temperature, it was poured into 1.5 l of water and ice under stirring.

After further 30 seconds of stirring, the precipitate was collected by filtration, washed with water till neutral pH and dried in the air.

The product was then recrystallized from isopropyl alcohol to yield 8 g of the desired product (compound No. 2), m.p. 145°-146° C. IR: significant bands at 1595, 1510, 1460, 1440, 1370 cm$^{-1}$.

EXAMPLE 3

Preparation of 2-(4-chlorophenyl)-3-(1,2,4-triazolyl-1)-4-ethoxycarboyl-5-phenyl-furan (Compound No. 3)

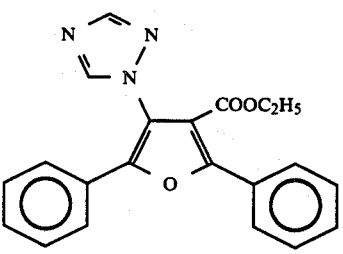

The compound was prepared with 82% of yield by operating in a way analogous to the one described in Example 1, starting from the ethyl ester of 2-benzoyl-3-(1,2,4-trimolyl-1)-3-(4-chlorophenyl)-propionic acid (described in Italian patent application No. 21.665 A/82).

Compound No. 3 was in the form of a crystalline solid having a m.p.=142°-144° C.

IR: significant bands at 1720, 1620, 1490, 1460, 1440 and 1220 cm$^{-1}$.

EXAMPLE 4

Determination of fungicidal activity against cucumber oidium [*Sphaerotheca fuliginea* (Schlech) Salmon].

Preventive activity:

Cucumber plants cv. Marketer, grown in pot in a conditioned environment, were sprayed on the lower leaf face with the product under examination in a water-acetone solution containing 20% C of acetone (vol/-vol). Then the plants were kept in a conditioned environment for 6 days and at the seventh day they were sprayed on the upper leaf face with an aqueous suspension of conidia of *Sphaerotheca fuligenea* (200.000 conidia/ml.). The plants were then carried back to the conditioned room. At the end of the incubation period of the fungus (8 days), the infection degree was evaluated by means of indexes of a scale of values from 100 (=sound plant) to 0 (=completely infected plant).

Curative activity:

Cucumber plants cv. Marketer, grown in pot in conditioned environment, were sprayed on the upper leaf face with an aqueous suspension of conidia of *Sphaerotheca fuliginea* (200.000 conidia/ml). After 24 hours from the infection the plants were treated with the product under examination in a water-acetone solution containing 20% of acetone (vol./vol.), by sprinkling both leaf faces.

At the end of the incubation period of the fungus (8 days), during which time the plants were kept in a suitably conditioned environment, the infection degree was evaluated by means of indexes of a scale of value from 100 (=sound plant) to 0 (=completely infected plant).

Compounds according to the invention showed a complete activity (100% reduction of the fungus infection) at doses 0.5 g/l, in tests having both preventive and curative characters. Furthermore, at lower doses as well, compounds according to the invention showed a high activity. For instance, Compound No. 1 (see example 1) still showed 100% of both curative and preventative activities, at the dose of 0.06 g/l.

What we claim is:

1. Compounds of formula

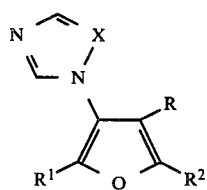
I wherein represents a nitrogen atom or a CH group;

R is selected from the group consisting of a hydrogen atom; an alkyl group having from 1 to 4 carbon atoms; an alkenyl or an alkynyl group having from 2 to 5 carbon atoms; an alkoxyl group having from 1 to 4 carbon atoms; a phenyl group or a phenoxy group optionally substituted by one or more groups selected from the group consisting of halogen atoms, alkyl groups having from 1 to 4 carbon atoms, alkoxyl groups having from 1 to 4 carbon atoms and a nitro group; an alkoxycarbonyl group having from 1 to 4 carbons in the alkoxy part, an alkylcarbonyl group having from 1 to 4 carbon atoms in the alkyl part; a benzoyl and a cyano group;

$R^1$ and $R^2$ (equal to or different from each other) are each selected from the group consisting of an alkyl group having from 1 to 4 carbon atoms; an alkenyl group or an alkynyl group having from 2 to 5 carbon atoms; a phenyl group optionally substituted by one or more groups selected from the group consisting of halogen atoms, alkyl groups having from 1 to 4 carbon atoms, alkoxyl groups having from 1 to 4 carbon atoms and a nitro group; an alkoxycarbonyl group having from 1 to 4 carbon atoms in the alkoxy part, an alkylcarbonyl group having from 1 to 4 carbon atoms in the alkyl part; a cyano group; or R and $R^2$ form together a benzene ring orthocondensed with the furan ring.

2. Compounds according to claim 1 wherein X is a nitrogen atom.

3. Compound 2,4,5-triphenyl-3-(1,2,4-triazolyl-1)-furan.

4. Compound 2,5-diphenyl-3-(1,2,4-triazolyl-1)-furan.

5. Compound 2-(4-chlorophenyl)-3-(1,2,4-triazolyl-1)-4-ethoxycarbonyl-5-phenyl-furan.

6. A method for fighting fungus infections in useful plants consisting in distributing on the plants or in the area where they grow, when the fungus infection is foreseen or it is in progress already, an effective amount of a compound according to claim 1, as such or in the form of a suitable composition.

7. A method for fighting fungus infections in useful plants, according to claim 6, applied to the fight against the fungus infections known as oidium and rust.

8. A fungicide composition having as active ingredient one or more compounds according to claim 1, together with a solid or liquid carrier and optionally other additives.

* * * * *